US012458390B2

(12) United States Patent
Nakamura

(10) Patent No.: US 12,458,390 B2
(45) Date of Patent: Nov. 4, 2025

(54) DRIVE DEVICE

(71) Applicant: OLYMPUS CORPORATION, Hachioji (JP)

(72) Inventor: Hiroto Nakamura, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 352 days.

(21) Appl. No.: 17/888,857

(22) Filed: Aug. 16, 2022

(65) Prior Publication Data

US 2022/0387066 A1 Dec. 8, 2022

Related U.S. Application Data

(63) Continuation of application No. PCT/JP2020/007683, filed on Feb. 26, 2020.

(51) Int. Cl.
*A61B 17/32* (2006.01)
*A61B 17/00* (2006.01)

(52) U.S. Cl.
CPC ................ *A61B 17/320068* (2013.01); *A61B 2017/00973* (2013.01)

(58) Field of Classification Search
CPC .. A61B 17/320068; A61B 2017/00973; A61B 17/32
See application file for complete search history.

(56) References Cited

U.S. PATENT DOCUMENTS 3,451,004 A * 6/1969 Norton, Jr. ................ H03F 1/20 330/54
3,946,738 A 3/1976 Newton et al.
2011/0299309 A1* 12/2011 Chen ..................... H03F 1/0294 363/37
2014/0180274 A1* 6/2014 Kabaya ............. A61B 18/1206 606/34
2020/0345406 A1 11/2020 Kato

FOREIGN PATENT DOCUMENTS

| | | | |
|---|---|---|---|
| JP | 663-073949 | A | 4/1988 |
| JP | 2003-299666 | A | 10/2003 |
| WO | 2019/146018 | A1 | 8/2019 |

OTHER PUBLICATIONS

Jun. 2, 2020 International Search Report issued in Patent Application No. PCT/JP2020/007683.
Oct. 10, 2023 Extended European Search Report issued in European Patent Application No. 20921143.2.

* cited by examiner

*Primary Examiner* — Gary L Laxton
(74) *Attorney, Agent, or Firm* — Oliff PLC

(57) ABSTRACT

A drive device includes: a first circuit including an alternating current (AC) power supply, a primary winding constituting a first side of an output transformer, and an input line connecting the primary winding and the AC power supply to each other; a second circuit including a pair of electrodes detachably connected to an ultrasound treatment instrument, a secondary winding constituting a second side of the output transformer, and a pair of output lines connecting the pair of electrodes and the secondary winding; and a pair of third circuits each having one end respectively connected to the output lines and another end connected to a ground. Each of the pair of third circuits includes an inductor being a passive element, and a capacitor being a passive element connected in series to the inductor. Each of the pair of third circuits is connected to each of the output lines.

18 Claims, 8 Drawing Sheets

DRIVE DEVICE

CROSS-REFERENCE TO RELATED APPLICATIONS

This application is a continuation of PCT international application No. PCT/JP2020/007683 filed on Feb. 26, 2020 which designates the United States. The entire content of which is incorporated herein by reference.

BACKGROUND

1. Technical Field

The present disclosure relates to a drive device that drives an ultrasound treatment instrument.

2. Related Art

There is a known treatment system that applies ultrasound oscillation to a biological tissue to treat the biological tissue.

A treatment system (ultrasound treatment device) that is known includes: an ultrasound treatment instrument that applies ultrasound oscillation to a biological tissue; and a drive device (ultrasound treatment device main body) that supplies drive power for driving the ultrasound treatment instrument to the ultrasound treatment instrument.

SUMMARY

In some embodiments, a drive device includes: a first circuit including an alternating current (AC) power supply, a primary winding constituting a first side of an output transformer, and an input line connecting the primary winding and the AC power supply to each other; a second circuit including a pair of electrodes detachably connected to an ultrasound treatment instrument, a secondary winding constituting a second side of the output transformer, and a pair of output lines connecting the pair of electrodes and the secondary winding to each other; and a pair of third circuits each having one end respectively connected to the pair of output lines and another end connected to a ground, each of the pair of third circuits being connected to each of the pair of output lines of the second circuit. Each of the third circuits includes an inductor being a passive element, and a capacitor being a passive element connected in series to the inductor.

In some embodiments, provided is a drive device configured to drive an ultrasound treatment instrument. The drive device includes: a first circuit including an alternating current (AC) power supply, a primary winding constituting a first side of an output transformer, and an input line connecting the primary winding and the AC power supply to each other; a second circuit including a pair of electrodes detachably connected to the treatment instrument, a secondary winding constituting a second side of the output transformer, and a pair of output lines connecting the pair of electrodes and the secondary winding to each other; and a pair of third circuits each having one end respectively connected to the pair of output lines and another end connected to a ground, each of the pair of third circuits being connected to each of the pair of output lines of the second circuit. Each of the third circuits includes an inductor being a passive element, and a capacitor being a passive element connected in series to the inductor.

The above and other features, advantages and technical and industrial significance of this disclosure will be better understood by reading the following detailed description of present embodiments of the disclosure, when considered in connection with the accompanying drawings.

DETAILED DESCRIPTION

Figure 1:
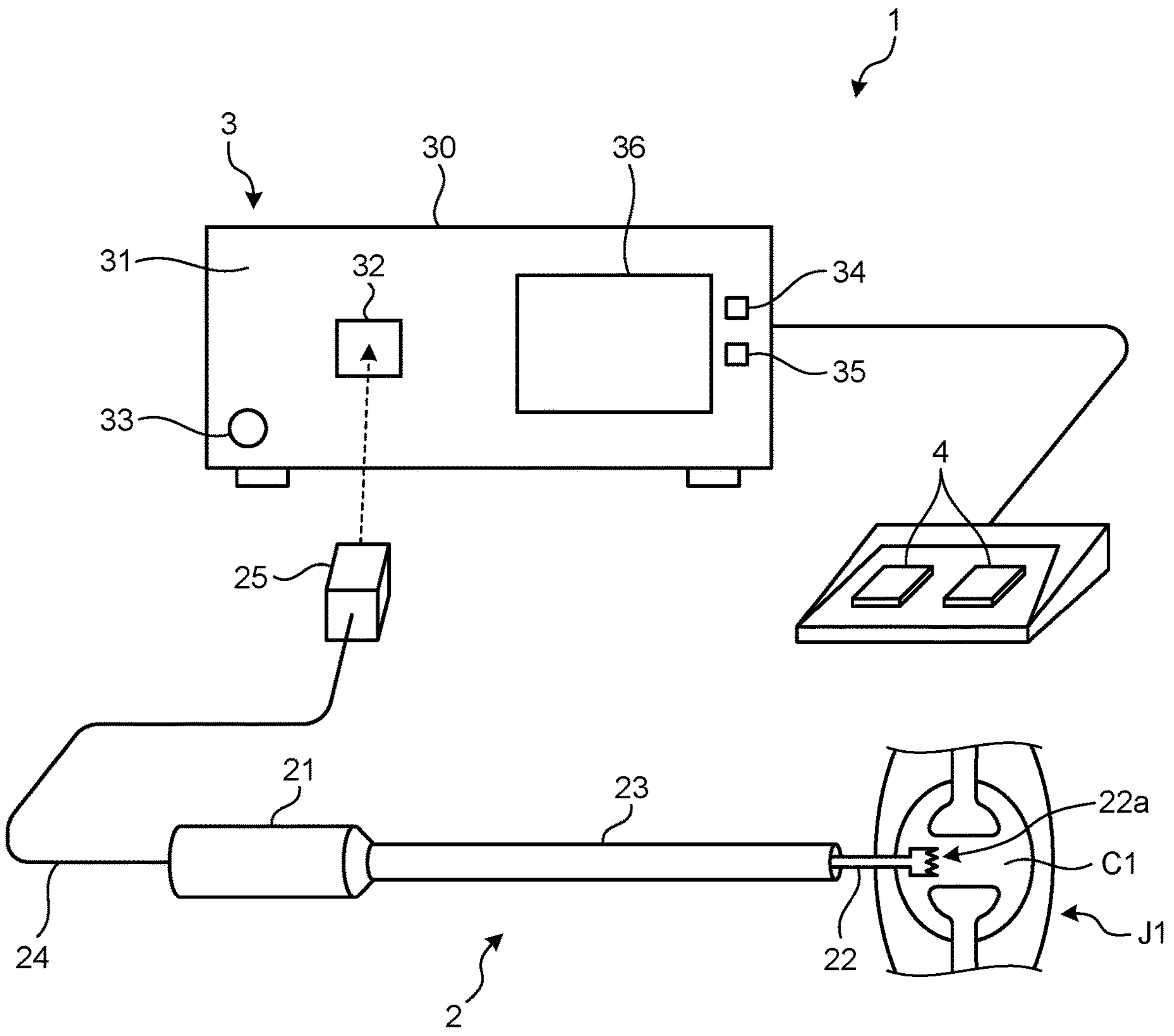
FIG. 1 is a diagram illustrating a schematic configuration of a treatment system according to an embodiment of the disclosure.

Hereinafter, modes (hereinafter, "embodiment") for carrying out the disclosure will be described with reference to the accompanying drawings. Note that the disclosure is not limited to embodiments described below. In the drawings, same reference signs are attached to the same components.

Schematic Configuration of Treatment System

FIG. 1 is a diagram illustrating a schematic configuration of a treatment system 1 according to the present embodiment.

The treatment system 1 applies ultrasound oscillation to a biological tissue such as a bone for treatment of the biological tissue. Here, the treatment includes removal or cutting of biological tissue such as bone, for example. Note that FIG. 1 illustrates, as the treatment system 1, a treatment system in which a distal end of a probe 22 constituting an ultrasound treatment instrument 2 is inserted into a joint space C1 of a knee joint J1 and an anterior cruciate ligament (ACL) reconstruction surgery is performed.

As illustrated in FIG. 1, the treatment system 1 includes the ultrasound treatment instrument 2, a drive device 3, and a foot switch 4.

As illustrated in FIG. 1, the ultrasound treatment instrument 2 includes a treatment instrument main body 21, the probe 22, a sheath 23, a cable 24, and a connector 25.

The treatment instrument main body 21 is formed in a cylindrical shape. The treatment instrument main body 21 internally houses: an ultrasound transducer 210 (refer to FIG. 2) constituted with a bolt-clamped Langevin-type transducer; and a drive energy input unit 200 (refer to FIG. 2) for driving the ultrasound transducer 210.

The probe 22 is formed in a substantially cylindrical shape. A proximal end portion of the probe 22 is connected to the treatment instrument main body 21. In addition, there is provided a treatment unit **22*a* at a distal end of the probe 22**.

The sheath 23 is formed in a cylindrical shape longer than the treatment instrument main body 21 and covers a part of an outer periphery of the probe 22 from the treatment instrument main body 21 to a certain length.

Inside the treatment instrument main body 21, the proximal end portion of the cable 24 is electrically connected to the drive energy input unit 200. The cable 24 is connected, at its distal end portion, with a connector 25.

The drive device 3 includes a casing 30 (FIG. 1) having a rectangular parallelepiped shape. The casing 30 internally houses a plurality of electronic components and the like constituting an electronic circuit and the like.

On a front surface portion 31 constituting the front surface of the casing 30, there are provided a connector 32, a power switch 33, two operation switches 34 and 35, and a display panel 36, which are provided in a state of being exposed to the outside. The connector 25 of the cable 24 of the ultrasound treatment instrument 2 is detachably connected to the connector 32. When the connector 25 and the connector 32 are connected to each other between the ultrasound treatment instrument 2 and the drive device 3, operations such as supply of drive power and communication of a control signal are performed via the cable 24.

In the treatment system 1 according to the present embodiment, in response to an output start operation to the foot switch 4 by an operator, drive power is supplied from the drive device 3 to the ultrasound treatment instrument 2. This allows the ultrasound treatment instrument 2 to generate ultrasound oscillation, leading to application of the ultrasound oscillation from the treatment unit 22*a* of the probe 22 to the biological tissue such as a bone. This enables treatment of the biological tissue such as the bone.

Circuit Configuration of Ultrasound Treatment Instrument and Drive Device

Figure 2:
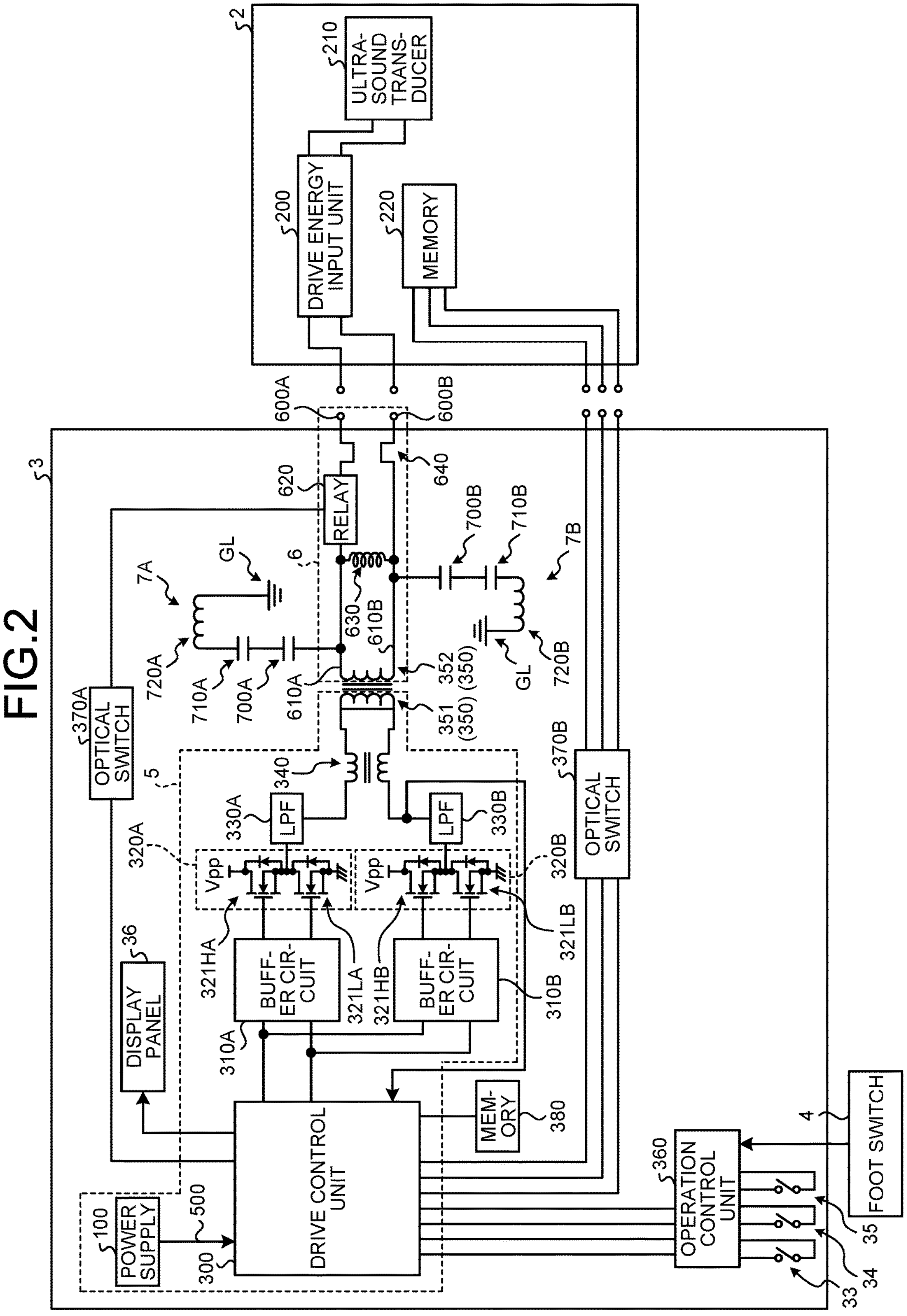
FIG. 2 is a block diagram illustrating a circuit configuration of an ultrasound treatment instrument and a drive device.

FIG. 2 is a block diagram illustrating a circuit configuration of the ultrasound treatment instrument 2 and the drive device 3.

As illustrated in FIG. 2, the ultrasound treatment instrument 2 includes a drive energy input unit 200, an ultrasound transducer 210, and memory 220. On the other hand, the drive device 3 includes a drive control unit 300, buffer circuits 310A and 310B, switching circuits 320A and 320B, low-pass filters 330A and 330B, a common mode coil 340, an output transformer 350, an operation control unit 360, optical switches 370A and 370B, and memory 380.

Next, the configurations of the above ultrasound treatment instrument 2 and the drive device 3 will be described together with the description of operations of the drive device 3.

When the operator performs an output start operation on the foot switch 4, a signal is input from the operation control unit 360 to the drive control unit 300. In response to the input of the signal, the drive control unit 300 controls the operation of a relay circuit 620 (FIG. 2) via the optical switch 370A to turn on the relay circuit 620. Additionally, in response to the input of the signal, the drive control unit 300 functions as a drive signal generator that generates a drive signal for driving the ultrasound treatment instrument 2 based on the power from the power supply 100. Subsequently, the drive control unit 300 outputs the drive signal to each of the switching circuits 320A and 320B via the buffer circuits 310A and 310B respectively. Here, the buffer circuits 310A and 310B are provided to reduce the load on the drive control unit 300 and increase the switching efficiency in the switching circuits 320A and 320B.

The switching circuit 320A includes a high-side switching element 321HA and a low-side switching element 321LA. Similarly, the switching circuit 320B includes a high-side switching element 321LB and a low-side switching element 321LB. In the following description, the four switching elements 321HA, 321HB, 321LA, and 321LB are also simply referred to as switching elements 321 when they are not particularly distinguished from each other. An example of applicable device for the switching element 321 is a field effect transistor (FET).

Based on the drive signals output from the buffer circuits 310A and 310B, the switching circuits 320A and 320B alternately turns on/off the high-side switching elements 321HA and 321HB and the low-side switching elements 321HA and 321HB at a frequency of the drive frequency of the ultrasound transducer 210 or more.

Outputs from the switching circuits 320A and 320B pass through the low-pass filters 330A and 330B and the common mode coil 340, respectively, and are then input to a primary winding 351 constituting one side of the output transformers 350. At this time, the outputs from the switching circuits 320A and 320B are converted into sinusoidal drive signals (hereinafter, referred to as an ultrasound drive signal) as a result of passing through the low-pass filters 330A and 330B. Here, the common mode coil 340 functions as a noise filter and reduces noise included in the ultrasound drive signal.

The devices according to the disclosure described above, namely, the power supply 100 having the function as an alternating current (AC) power supply, the primary winding 351, an input line 500 connecting the primary winding 351 and the power supply 100 to each other, as well as devices provided on the input line 500, namely, the drive control unit 300, the buffer circuits 310A and 310B, the switching circuits 320A and 320B, the low-pass filters 330A and 330B, the common mode coil 340, constitute a first circuit 5 (FIG. 2).

When a sinusoidal ultrasound drive signal has been input to the primary winding 351, an ultrasound drive signal stepped up from the primary winding 351 is output to a secondary winding 352 constituting the other side of the output transformers 350. The ultrasound drive signal is AC power generated in a second circuit 6 to be described below and output to the ultrasound treatment instrument 2, and this power in the present embodiment is relatively high AC power of 100 W or more and 400 W or less.

Here, as illustrated in FIG. 2, the connector 32 has a pair of electrodes 600A and 600B, which is electrically connected to the drive energy input unit 200 via the cable 24 when the connector 32 and the connector 25 are connected to each other. The pair of electrodes 600A and 600B are connected to the secondary winding 352 respectively through a pair of output lines 610A and 610B.

The above-described devices, namely, the pair of electrodes 600A and 600B, the secondary winding 352, and the pair of output lines 610A and 610B, constitute the second circuit 6 (FIG. 2). The second circuit 6 is also referred to as a patient circuit. That is, the second circuit 6 is a circuit that is electrically insulated from the first circuit 5 by the output transformer 350 and is also electrically insulated from the ground. As illustrated in FIG. 2, the second circuit 6 according to the present embodiment further includes a relay circuit 620, a matching coil 630, and an anti-noise component 640.

The relay circuit 620 is provided on the output line 610A. Under the control of the drive control unit 300, the relay circuit 620 is switched on/off, that is, between an on state in which the secondary winding 352 and the pair of electrodes 600A and 600B are brought into electrical conduction and an off state in which the secondary winding 352 and the pair of electrodes 600A and 600B are brought into non-electrical conduction. That is, when the relay circuit 620 is in the on state, the ultrasound drive signal output to the secondary winding 352 is transmitted to the pair of electrodes 600A and 600B via the pair of output lines 610A and 610B, respectively. In contrast, when the relay circuit 620 is in the off state, the ultrasound drive signal output to the secondary winding 352 is not transmitted to the pair of electrodes 600A and 600B via the pair of output lines 610A and 610B, respectively.

The matching coil 630 is provided in a state of connecting the pair of output lines 610A and 610B to each other, and is used to efficiently drive the ultrasound transducer 210. In the present embodiment, the matching coil 630 is provided on the secondary winding 352 side of the relay circuit 620. However, the position is not limited thereto, and the matching coil 630 may be provided at other positions.

The anti-noise component 640 includes, for example, a ferrite core or the like, and is provided on the pair of electrodes 600A and 600B side of the relay circuit 620 and the matching coil 630. The anti-noise component 640 is a component that prevents unnecessary noise output from the pair of electrodes 600A and 600B from affecting an external device disposed close to the treatment system 1.

In addition, in the present embodiment, as illustrated in FIG. 2, third circuits 7A and 7B are connected to the pair of output lines 610A and 610B, respectively.

The configurations and functions of the third circuits 7A and 7B will be described in "Configuration of third circuit" and "Functions of third circuit" described below.

The ultrasound drive signal output to the secondary winding 352 is output to the drive energy input unit 200 via the second circuit 6, the connector 25, and the cable 24. Subsequently, in response to the input of the ultrasound drive signal, the drive energy input unit 200 causes the ultrasound transducer 210 to implement ultrasound oscillation.

In addition, the drive control unit 300 is connected to the memory 220 of the ultrasound treatment instrument 2 via the optical switch 370B, and reads ID information of the ultrasound treatment instrument 2 stored in the memory 220 to determine the type or the like of the ultrasound treatment instrument 2. Furthermore, based on the information stored in the memory 380, the drive control unit 300 sets drive parameters (basic frequency, current value, maximum continuous output time, etc.) according to the determined type of the ultrasound treatment instrument 2. Subsequently, the drive control unit 300 generates a drive signal based on a feedback result of the voltage and the current of the ultrasound drive signal.

In addition, the drive control unit 300 controls the display panel 36 to display the magnitude of the ultrasound drive signal output from the drive device 3 to the ultrasound treatment instrument 2. The magnitude of the ultrasound drive signal output from the drive device 3 to the ultrasound treatment instrument 2 can be adjusted by operating the foot switch 4, the operation switches 34 and 35, and the like.

Configuration of Third Circuit

Next, the configuration of the third circuits 7A and 7B will be described with reference to FIG. 2.

The third circuit 7A has one end electrically connected to the output line 610A, and the other end electrically connected to a ground GL. In the present embodiment, in the output line 610A, one end of the third circuit 7A is connected to the secondary winding 352 side of the relay circuit 620, the matching coil 630, and the anti-noise component 640. The third circuit 7A has a configuration in which capacitors 700A and 710A being passive elements and an inductor 720A being a passive element are connected in series. In the present embodiment, capacitors 700A, 710A and inductor 720A are arranged in this order along a direction from output line 610A to the ground GL.

Here, the inductor 720A corresponds to a first passive element. The capacitors 700A and 710A correspond to a second passive element.

One end of the third circuit 7B is electrically connected to the output line 610B, and the other end is electrically connected to the ground GL. In the present embodiment, one end of the third circuit 7B is connected to the secondary winding 352 side of the matching coil 630 and the anti-noise component 640 in the output line 610B. The third circuit 7B has a configuration in which capacitors 700B and 710B being passive elements and an inductor 720B being a passive element are connected in series. In the present embodiment, the capacitors 700B, 710B and the inductor 720B are arranged in this order in the direction from the output line 610B to the ground GL.

Here, the inductor 720B corresponds to a first passive element. The capacitors 700B and 710B correspond to a second passive element.

In the present embodiment, the capacitance of each of the capacitors 700A, 710A, 700B, and 710B is 1 pF or more and 100 nF or less.

The third circuits 7A and 7B described above are connected to the pair of output lines 610A and 610B respectively with a paired configuration. Here, "paired configuration" means that there is identicalness, between the third circuit 7A and the third circuit 7B, in the number of capacitors (two in the present embodiment), the number of inductors (one in the present embodiment), and the arrangement order of the capacitors and the inductors from the output lines 610A and 610B to the ground GL. That is, the third circuit 7A and the third circuit 7B need not have the same specifications such as the capacitance of the capacitor or the inductor.

Functions of Third Circuit

Figure 3:
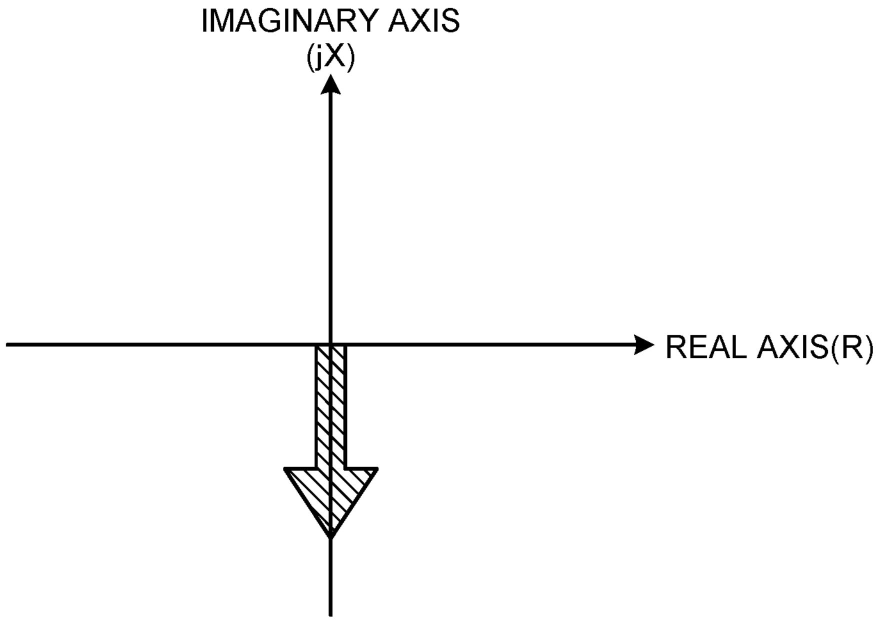
FIG. 3 is a diagram illustrating functions of a third circuit.
Figure 4:
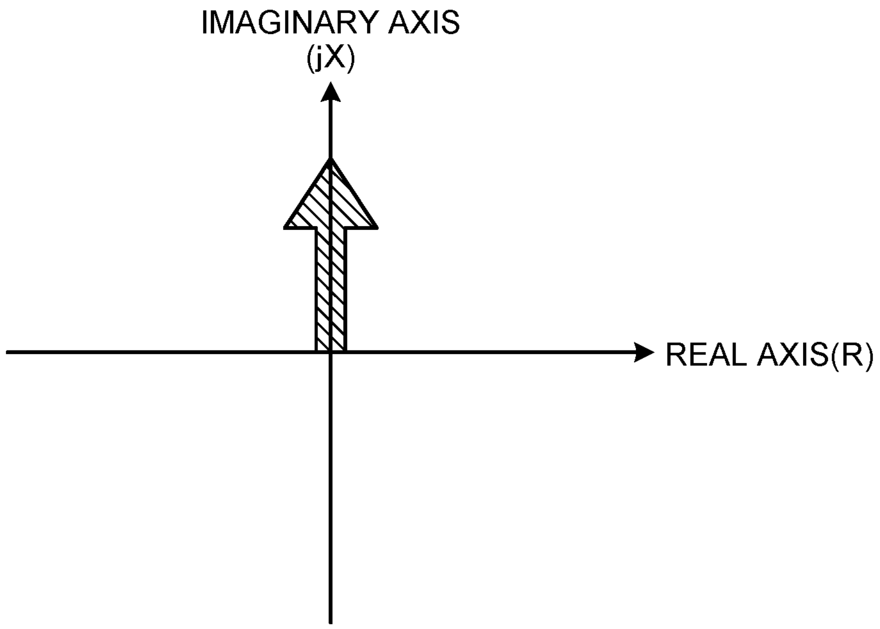
FIG. 4 is a diagram illustrating functions of the third circuit.

FIGS. 3 and 4 are diagrams illustrating functions of the third circuits 7A and 7B.

Next, functions of the third circuits 7A and 7B will be described with reference to FIGS. 3 and 4.

The current (hereinafter, described as patient leakage current) leaking from the second circuit 6 depends on a stray capacitance of a component such as the output transformer 350 used for electrical insulation of the second circuit 6 or a stray capacitance due to a circuit pattern. That is, the higher the stray capacitance, the higher the patient leakage current. In addition, the patient leakage current needs to be measured by the second circuit 6, and the higher the value of the ultrasound drive signal (AC power) output to the ultrasound treatment instrument 2, the higher the patient leakage current becomes.

The inductors 720A and 720B constituting the third circuits 7A and 7B have a function of reducing the patient leakage current by apparently lowering the stray capacitance described above.

Specifically, impedance $Z_C$ of the stray capacitance (capacitor component) is expressed by $1/j\omega C$ when an imaginary unit is j, an angular frequency of alternating current is ω, and capacitance is C. That is, the impedance $Z_C$ is a downward vector in a complex plane as indicated by an arrow in FIG. 3.

On the other hand, the impedance $Z_L$ of the inductors 720A and 720B is expressed by $j\omega L$ when an imaginary unit is j, an angular frequency of alternating current is ω, and inductance is L. That is, the impedance $Z_L$ is a vector directed upward in a complex plane as indicated by an arrow in FIG. 4.

Therefore, by providing the inductors 720A and 720B, it is possible to cancel the influence of the stray capacitance (capacitor component) described above (possible to apparently decrease the stray capacitance described above), leading to achievement of reduction in the patient leakage current.

The capacitors 700A and 710A constituting the third circuit 7A are used for apparent electrical insulation of the second circuit 6 and the ground GL from each other.

The present embodiment described above achieves the following effects.

Figure 5:
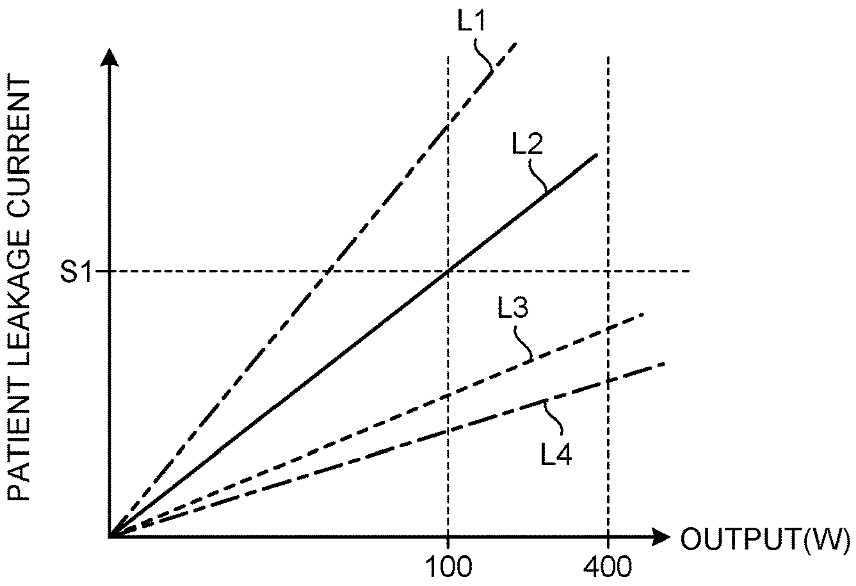
FIG. 5 is a diagram illustrating an effect of the embodiment.

FIG. 5 is a diagram illustrating an effect of the present embodiment. Specifically, FIG. 5 is a graph in which the horizontal axis represents the value of the ultrasound drive signal (AC power) generated in the second circuit 6 and output to the ultrasound treatment instrument 2, while the vertical axis represents the value of the patient leakage current measured by the output lines 610A and 610B. In FIG. 5, line L1 indicates a relationship, unlike the present embodiment, between the ultrasound drive signal to be output to the ultrasound treatment instrument 2 and the patient leakage current in a case where the inductors 720A and 720B are omitted from and the capacitors 700A, 710A, 700B, and 710B are left in the third circuits 7A and 7B. Line L2 indicates the above-described relationship in a case where the third circuits 7A and 7B are not provided, unlike the present embodiment. Line L3 indicates the above-described relationship in a case where the third circuits 7A and 7B are provided similarly to the present embodiment. Line L4 indicates the above-described relationship in a case where the capacitors 700A, 710A, 700B, and 710B are omitted from and the inductors 720A and 720B are left in the third circuits 7A and 7B, unlike the present embodiment.

In a case where the inductors 720A and 720B are omitted from the third circuits 7A and 7B and the capacitors 700A, 710A, 700B, and 710B are left, the value of the patient leakage current exceeds a standard value S1 defined in the safety standard before the value of the ultrasound drive signal output to the ultrasound treatment instrument 2 becomes 100 W as indicated by line L1 in FIG. 5.

In addition, when the third circuits 7A and 7B are not provided, as indicated by line L2 in FIG. 5, when the value of the ultrasound drive signal generated in the second circuit 6 and output to the ultrasound treatment instrument 2 is less than 100 W, the value of the patient leakage current can be set to a value that does not exceed the standard value S1 defined in the safety standard. However, when the value of the ultrasound drive signal output to the ultrasound treatment instrument 2 is 100 W or more as in the present embodiment having a relatively hard biological tissue such as a bone as a treatment target, the value of the patient leakage current would exceed the standard value S1.

In order to suppress this, the present embodiment is provided with the third circuits 7A and 7B. Therefore, as indicated by line L3 in FIG. 5, even when the value of the ultrasound drive signal output to the ultrasound treatment instrument 2 is 100 W or more, the value of the patient leakage current can be set to the standard value S1 or less.

Therefore, according to the drive device 3 of the present embodiment, the patient leakage current can be reduced even when the output to the ultrasound treatment instrument 2 is high.

Furthermore, the similar applies to a case where the value of the ultrasound drive signal output to the ultrasound treatment instrument 2 is 400 W or less.

In addition, with the presence of the passive elements in the third circuits 7A and 7B, it is possible to sufficiently reduce the patient leakage current with a simple configuration. The passive element can reduce patient leakage current without active control unlike the active element. Therefore, by incorporating the value of the passive element at the time of assembling the drive device 3, the patient leakage current can be reduced with a simple configuration. The constant of the passive element is determined in consideration of the output and the circuit configuration. For example, when the output is 200 W and the circuit configuration of the present embodiment is adopted, the capacitor may be set to 1 nF and the inductor may be set to 150 mH.

Furthermore, the passive element has a small number of components, and thus can reduce patient leakage current at low cost. In addition, the passive element is space-saving, enabling downsizing of the drive device 3.

OTHER EMBODIMENTS

While the above is description of the modes for carrying out the disclosure, the disclosure should not be limited by only the embodiments described above.

Figure 6:
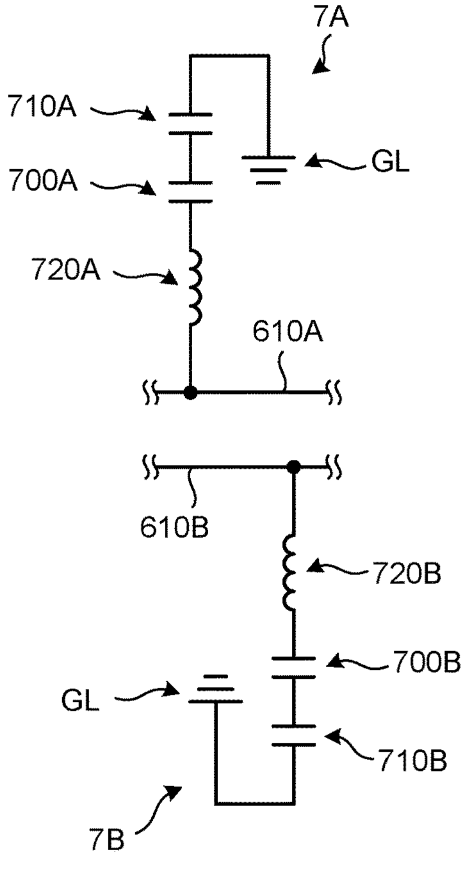
FIG. 6 is a view illustrating a modification of the embodiment.
Figure 7:
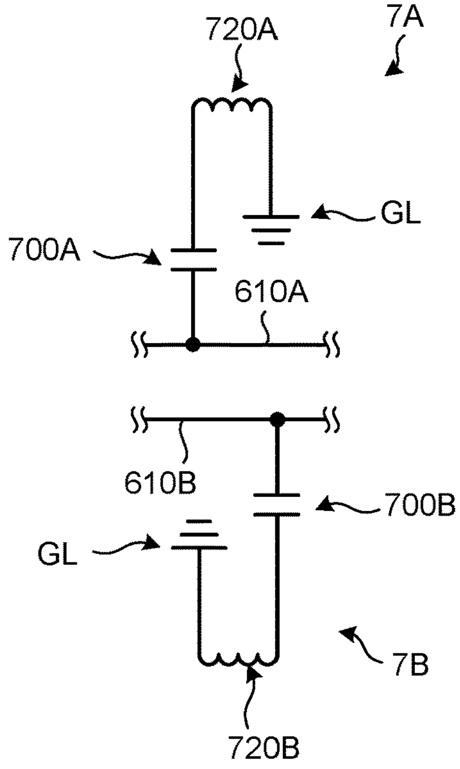
FIG. 7 is a view illustrating a modification of the embodiment.
Figure 8:
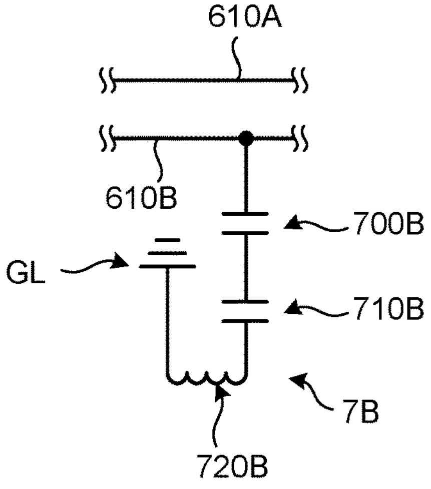
FIG. 8 is a view illustrating a modification of the embodiment.

FIGS. 6 to 8 are views illustrating a modification of the present embodiment.

In the third circuit according to the disclosure, the arrangement order of the inductors and the capacitors is not limited to the arrangement order described in the above-described embodiment, and other arrangement orders may be adopted.

As compared to the third circuits 7A and 7B described in the above-described embodiment, an example illustrated in FIG. 6 is an example in which the arrangement order of the inductor 720A and the capacitors 700A and 710A is changed, and the arrangement order of the inductor 720B and the capacitors 700B and 710B is changed in a similar manner.

In addition, in the third circuit according to the disclosure, the number of inductors and capacitors is not limited to the above-described number, and other numbers may be adopted.

The example illustrated in FIG. 7 is an example in which the capacitors 710A and 710B are omitted from the third circuits 7A and 7B described in the above-described embodiment. In this case, decreased number of capacitors leads to the small number of components, making it possible to achieve cost reduction and simplification of circuit patterns.

In the above-described embodiment, the third circuit according to the disclosure is connected to each of the pair of output lines 610A and 610B. The disclosure is not limited thereto, and one of the pair of output lines 610A and 610B may be omitted.

The example illustrated in FIG. 8 is an example including the third circuit 7B alone. This configuration enables adjustment when the patient leakage current is biased to one output line. In addition, since fewer numbers of capacitors and the number of inductors are used compared with the above-described embodiment, making it possible to reduce the number of components and the cost, leading to the simplification of the circuit patterns.

In the above-described embodiment, the following configuration may be adopted.

Figure 9:
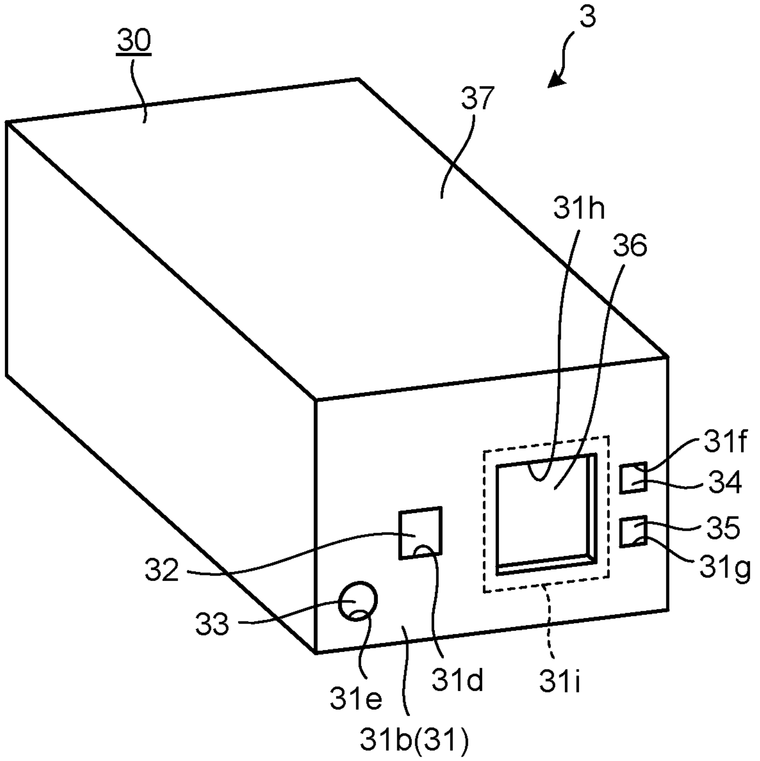
FIG. 9 is a view illustrating a modification of the embodiment.
Figure 10:
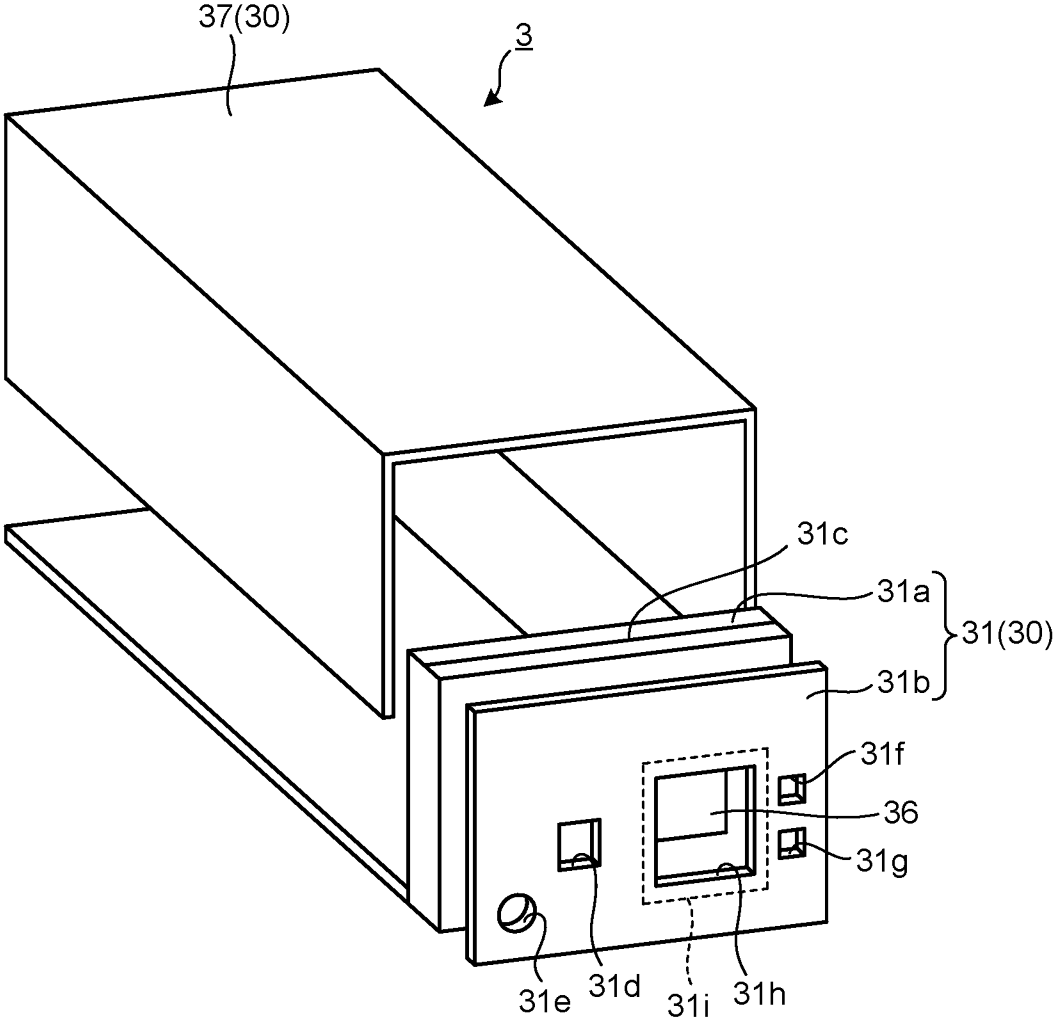
FIG. 10 is a view illustrating a modification of the embodiment.
Figure 11:
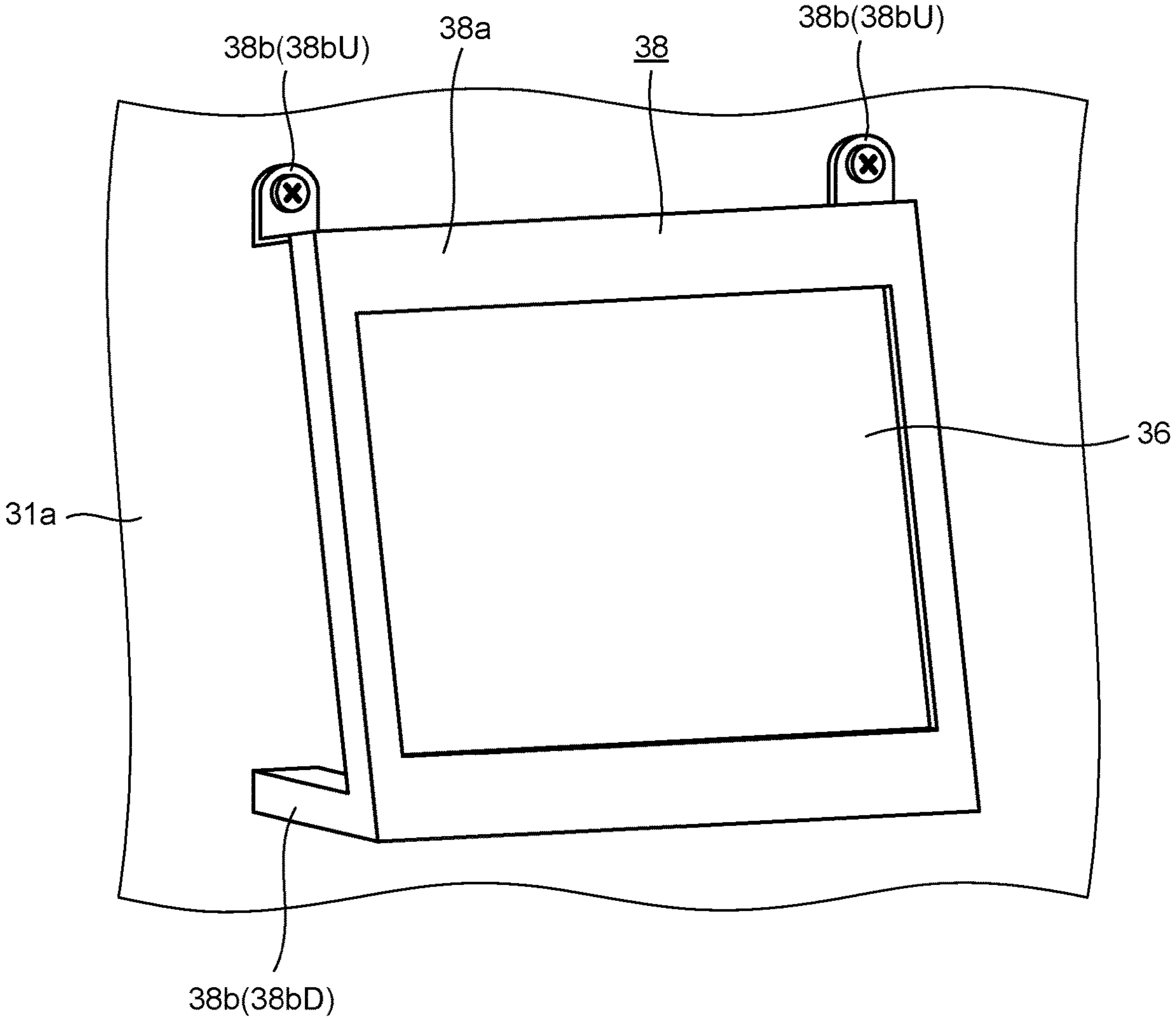
FIG. 11 is a view illustrating a modification of the embodiment.

A case in which the circuit of the disclosure is housed will be described with reference to FIGS. 9 to 11. Specifically, FIG. 9 is a perspective view of the drive device 3 as viewed from the front (side of the front surface portion 31). FIG. 10 is an exploded perspective view of the casing 30 constituting the drive device 3. FIG. 11 is a perspective view of a support member 38 as viewed from the front of casing 30.

As illustrated in FIG. 9 or 10, the front surface portion 31 includes a front panel 31*a* (FIG. 10) and a front panel cover 31*b*.

The front panel 31*a* is formed with a plate body having a rectangular shape when viewed from the front surface. The front panel 31*a* is a panel to which the connector 32, the power switch 33, the two operation switches 34 and 35, the display panel 36, and the like are assembled.

As illustrated in FIG. 10, a gasket 31*c* is attached to the upper end of the front panel 31*a* over the entire length of the upper end. When a U-shaped top cover 37 constituting the upper surface and the pair of side surfaces of the casing 30 is assembled to the front panel 31*a*, the gasket 31*c* comes in contact with an inner surface of the top cover 37. This eliminates a gap between the front panel 31*a* and the top cover 37 leading to the improvement of the watertightness.

Here, as illustrated in FIG. 11, the display panel 36 is assembled to the front panel 31*a* while being supported by the support member 38.

The support member 38 includes: a frame body 38*a* having a rectangular frame shape and surrounding the outer edge of the display panel 36; and four legs 38*b* protruding from four corners of the frame body 38*a* toward the back surface side and attached to the front surface of the front panel 31*a*. Note that, for convenience of description, FIG. 11 illustrates only one of two legs 38*b*D, which are lower legs out of the four legs 38*b*.

Here, among the four legs 38*b*, two legs 38*b*U, which are upper legs, have a shorter protrusion length than the two lower legs 38*b*D. That is, when the support member 38 is attached to the front surface of the front panel 31*a*, the display panel 36 is in a posture inclined toward the front surface as it goes downward. This makes it possible to achieve a structure in which a liquid such as a medical agent flows only in a predetermined direction (the bottom surface side of the casing 30) even if a waterproof tape 31*i* is damaged. Note that, although not specifically illustrated, there is no circuit board at a position to which a liquid flows. This prevents the circuit board from getting wet.

The front panel cover 31*b* is formed with a rectangular plate body when viewed from the front surface, and covers the front surface of the front panel 31*a*. The front panel cover 31*b* is provided with apertures 31*d* to 31*h* for exposing the connector 32, the power switch 33, the two operation switches 34 and 35, and the display panel 36 respectively to the outside.

On the back surface of the front panel cover 31*b*, the waterproof tape 31*i*, having a rectangular shape, is attached around an aperture 31*h* for exposing the display panel 36 to the outside. When the front panel cover 31*b* is assembled to the front panel 31*a*, the waterproof tape 31*i* comes in contact with the front surface of the support member 38 to which the display panel 36 is fixed. This makes it possible to eliminate a gap between the front panel cover 31*b* and the support member 38 to which display panel 36 is fixed, leading to improvement in the watertightness.

In addition, by bringing the waterproof tape 31*i* into contact with the front panel cover 31*b* and the support member 38 via the waterproof tape 31*i*, even when the support member 38 expands and contracts due to the influence of temperature change, distortion is absorbed by the waterproof tape 31*i*, leading to suppression of occurrence of distortion in the front panel cover 31*b*.

According to the drive device of the disclosure, it is possible to reduce the patient leakage current even when the output to the ultrasound treatment instrument is high.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A drive device comprising:
- a first circuit including:
  - an alternating current (AC) power supply,
  - a drive control unit,
  - a primary winding constituting a first side of an output transformer, and
- a second circuit including:
  - a pair of electrodes detachably connected to an ultrasound treatment instrument,
  - a secondary winding constituting a second side of the output transformer,
  - a pair of output lines connecting the pair of electrodes and the secondary winding to each other, and
  - a matching coil; and
- a pair of third circuits each having one end respectively connected to the pair of output lines and another end connected to a ground, each of the pair of third circuits being connected to each of the pair of output lines of the second circuit, each of the third circuits including:
  - an inductor being a passive element, and
  - a capacitor being a passive element connected in series to the inductor in a corresponding one of the third circuits,
- wherein the pair of third circuits are arranged between the matching coil and the secondary winding.

2. The drive device according to claim 1, wherein the capacitor in each third circuit is provided as two or more capacitors connected in series.

3. The drive device according to claim 1, wherein a capacitance of each capacitor is 1 pF or more and 100 nF or less.

4. The drive device according to claim 1, wherein AC power generated in the second circuit and output to the ultrasound treatment instrument is 100 W or more and 400 W or less.

5. A drive device configured to drive an ultrasound treatment instrument, the drive device comprising:
- a first circuit including:
  - an alternating current (AC) power supply,
  - a drive control unit,
  - a primary winding constituting a first side of an output transformer, and
- a second circuit including:
  - a pair of electrodes detachably connected to the treatment instrument,
  - a secondary winding constituting a second side of the output transformer,
  - a pair of output lines connecting the pair of electrodes and the secondary winding to each other, and
  - a matching coil; and
- a pair of third circuits each having one end respectively connected to the pair of output lines and another end connected to a ground, each of the pair of third circuits being connected to each of the pair of output lines, each of the pair of third circuits including:

a first passive element configured to lower a stray capacitance of the drive device, and a second passive element connected in series to the first passive element, the second passive element electrically insulating the second circuit and the ground from each other in a corresponding one of the third circuits, wherein the pair of third circuits are arranged between the matching coil and the secondary winding.

6. The drive device according to claim 1, wherein in each one of the third circuits, the inductor is arranged between the ground and the capacitor.

7. The drive device according to claim 1, wherein in each one of the third circuits, the capacitor is arranged between the ground and the inductor.

8. The drive device according to claim 7, wherein the first passive element of each of the pair of third circuits is an inductor, the second passive element of each of the pair of third circuits is a capacitor, the capacitor in each third circuit is provided as two or more capacitors connected in series.

9. The drive device according to claim 7, wherein the first passive element of each of the pair of third circuits is an inductor, the second passive element of each of the pair of third circuits is a capacitor, a capacitance of each capacitor of the pair of third circuits is 1 pF or more and 100 nF or less.

10. The drive device according to claim 7, wherein AC power generated in the second circuit and output to the ultrasound treatment instrument is 100 W or more and 400 W or less.

11. The drive device according to claim 7, wherein in each one of the third circuits, the first passive element is arranged between the ground and the second passive element.

12. The drive device according to claim 7, wherein in each one of the third circuits, the second passive element is arranged between the ground and the first passive element.

13. A drive device comprising:

a first circuit including:

an alternating current (AC) power supply, a drive control unit, and a primary winding constituting a first side of an output transformer, a second circuit including:

a pair of electrodes detachably connected to an ultrasound treatment instrument, a secondary winding constituting a second side of the output transformer, a pair of output lines connecting the pair of electrodes and the secondary winding to each other, and a matching coil; and a third circuit having one end connected to one of the pair of output lines and another end connected to a ground, the third circuit including:

an inductor being a passive element, and a capacitor being a passive element connected in series to the inductor, wherein the third circuit is arranged between the matching coil and the secondary winding.

14. The drive device according to claim 13, wherein the capacitor is provided as two or more capacitors connected in series.

15. The drive device according to claim 13, wherein a capacitance of the capacitor is 1 pF or more and 100 nF or less.

16. The drive device according to claim 13, wherein AC power generated in the second circuit and output to the ultrasound treatment instrument is 100 W or more and 400 W or less.

17. The drive device according to claim 13, wherein the inductor is arranged between the ground and the capacitor.

18. The drive device according to claim 13, wherein the capacitor is arranged between the ground and the inductor.

* * * * *